United States Patent [19]

Baldacci et al.

[11] Patent Number: 5,416,942
[45] Date of Patent: May 23, 1995

[54] MOTORIZED ANTI-PLAQUE TOOTHBRUSH

[75] Inventors: Lapo Baldacci, Florence; Enzo Galantini, Modena, both of Italy

[73] Assignee: Ariete S.r.l., Italy

[21] Appl. No.: 194,008

[22] Filed: Feb. 9, 1994

[30] Foreign Application Priority Data

Feb. 26, 1993 [IT] Italy ............... GE93A0014

[51] Int. Cl.6 .............. A61C 17/34; A46B 13/02
[52] U.S. Cl. ........................ 15/22.1; 15/28
[58] Field of Search ............ 15/22.1, 22.2, 28, 29

[56] References Cited

U.S. PATENT DOCUMENTS

| 4,079,517 | 3/1978 | Zacharia | 15/28 X |
| 4,371,341 | 2/1983 | Nakanishi | 433/118 |
| 4,989,287 | 2/1991 | Scherer | 15/22.1 |

FOREIGN PATENT DOCUMENTS 0357863  3/1990  European Pat. Off.
324221   5/1970  Sweden ............ 15/22.1
92/19177 11/1992  WIPO .

Primary Examiner—Edward L. Roberts, Jr.
Attorney, Agent, or Firm—Larson and Taylor

[57] ABSTRACT

A motorized anti-plaque toothbrush comprises a handle (1) at one end of which is a cleaning/massaging head (3), in particular a brushing head, which rotates about an axis which is approximately perpendicular to the longitudinal axis of the handle (1) and is turned with a continuous one-way rotary motion or with a reciprocating rotary motion by a motor, preferably an electric motor, housed in the handle (1). According to the invention, the cleaning/massaging head (3) is composed of at least two separate cleaning/massaging tool parts (4, 5) that are supported coaxially with respect to each other in such a way that they can rotate relative to each other, being turned in mutually opposite directions in the case of continuous one-way rotation and in phase opposition to each other in the case of reciprocating rotation.

15 Claims, 4 Drawing Sheets

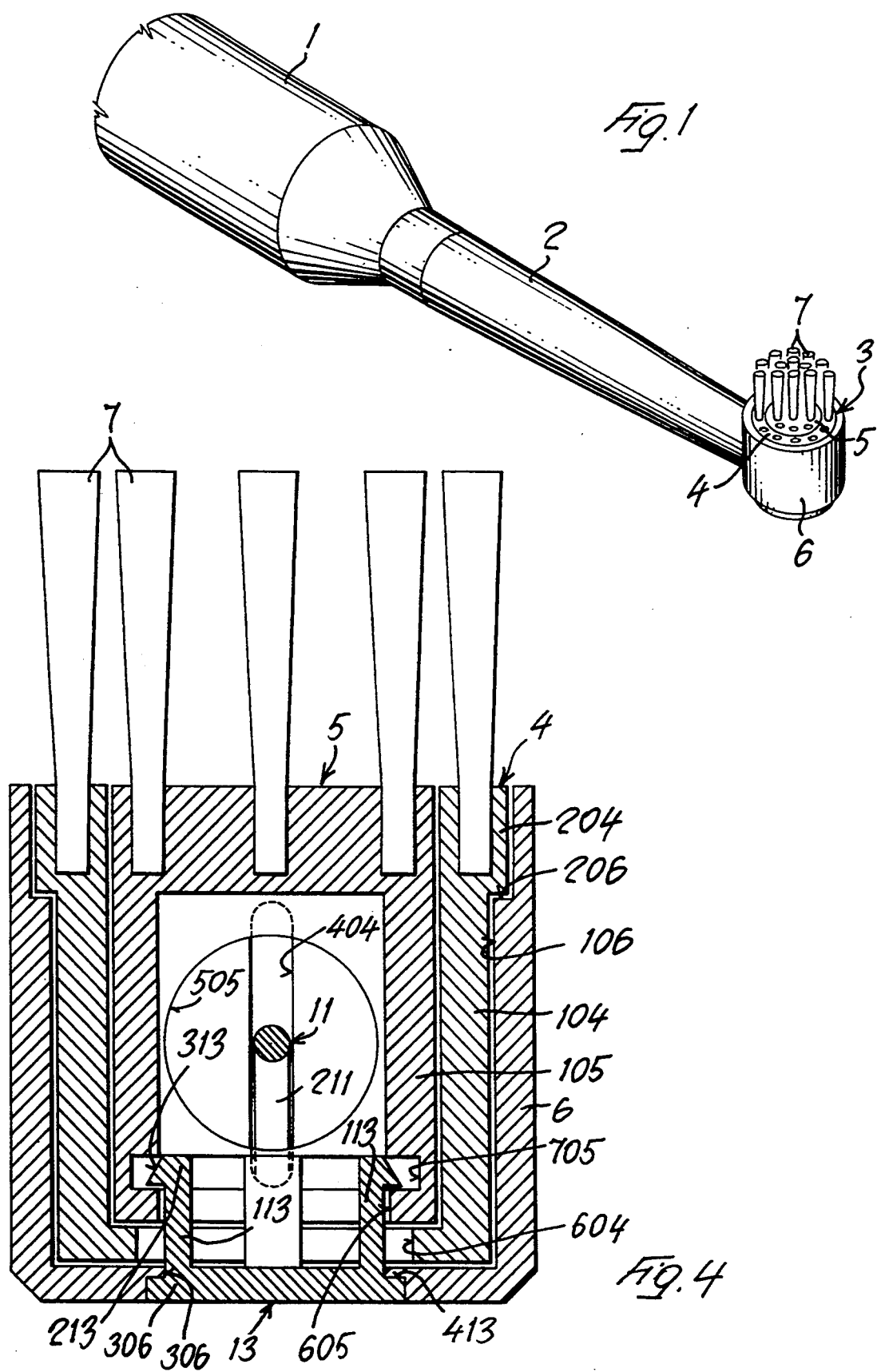

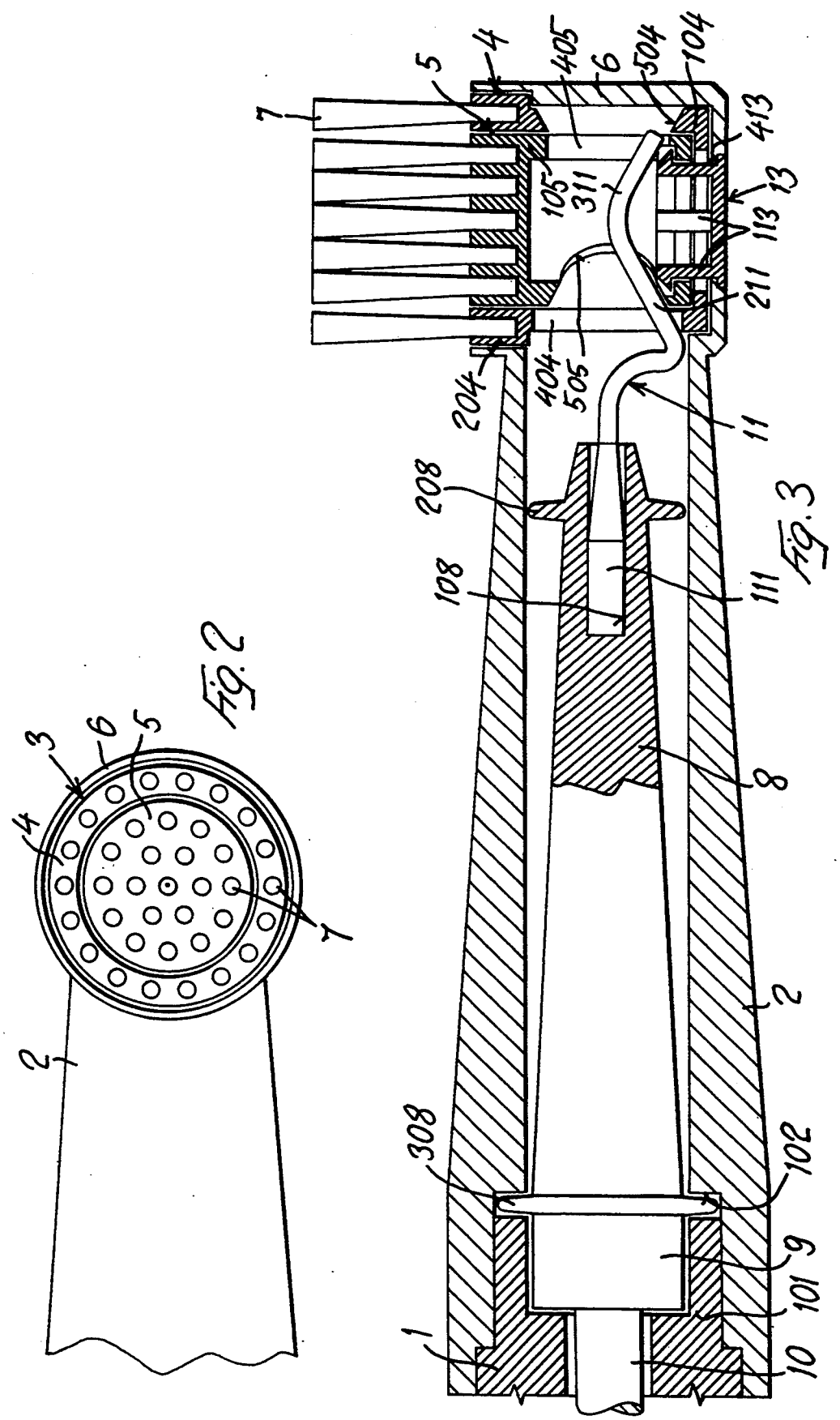

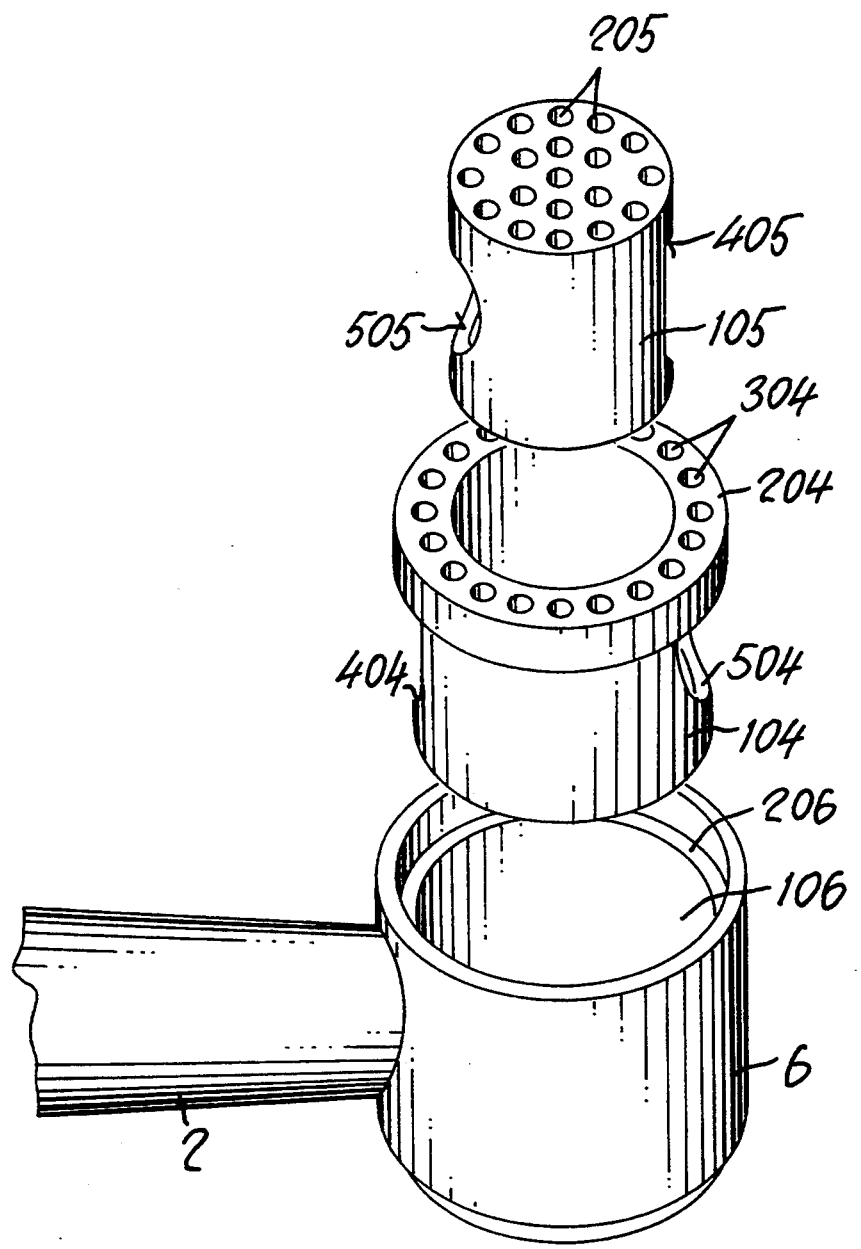
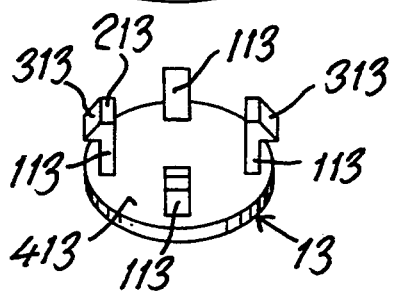
Fig. 5

MOTORIZED ANTI-PLAQUE TOOTHBRUSH

BACKGROUND AND SUMMARY OF THE INVENTION

The invention relates to a motorized anti-plaque toothbrush comprising a handle at one end of which is a cleaning/massaging head, in particular a brushing head, which rotates about an axis which is approximately perpendicular to the longitudinal axis of the handle and is turned with a continuous one-way rotary motion or with a reciprocating rotary motion by a motor, preferably an electric motor, housed in the handle.

The object of the invention is to provide a toothbrush of the type described above that will provide a more effective cleaning action and plaque-removal action, while at the same time, guaranteeing excellent treatment of the gingivae from the point of view of massaging and cleaning of the gingivae.

A further object is to improve the construction of a toothbrush of the type described at the outset in such a way that the drive parts and transmission parts, in particular, are easier to produce and assemble so that manufacturing costs are lower and the toothbrush is longer-lasting.

The invention achieves these objects in the form of a toothbrush of the type described at the outset, in which the cleaning/massaging head is composed of at least two separate cleaning/massaging tool parts that are supported coaxially with respect to each other in such a way that they can rotate relative to each other, being turned in mutually opposite directions in the case of continuous one-way rotation and in phase opposition to each other in the case of reciprocating rotation.

The rotary drive means and the cleaning/massaging tools may be of any type.

In the case of a brushing head, this head is composed of at least one tubular outer brush and at least one central inner brush that is coaxial with and rotates relative to the tubular outer brush, the bristles of both brushes lying generally parallel to the axis of rotation or of oscillation.

The free ends of the bristles of the tubular outer brush and central inner brush may terminate on the same flat or curved surface or they may be of different lengths from each other.

The two contrarotating parts of the brushing head give enhanced cleaning action and plaque-removing action. The advantageous gingivae messaging action is also improved.

According to a further characteristic of the invention, the means for turning the two coaxial brushes in a reciprocating manner in phase opposition to each other comprise:

a drive shaft that rotates continuously in one direction about its axis, which is perpendicular to the axis of rotation of the brushes; and transmission means that transmit the rotary motion to the brushes and consist of a transmission spindle coupled in rotation to the drive shaft and dynamically engaged with both brush parts, being shaped in such a way that the two brush parts oscillate about their common axis of rotation between two extreme angular positions in phase opposition to each other.

The transmission spindle is made in the form of a shaft with bends.

In a particularly advantageous embodiment of the invention, the transmission spindle comprises an eccentric V-shaped segment oriented transversely to the axis of rotation of the drive shaft with its vertex more or less in the axis of rotation of the two coaxial brushes, while the tubular outer brush and the inner brush are provided with cylindrical bristle-carrying bases supported rotatably about their axis one inside the other, said bristle-carrying bases each being provided on diametrically opposite sides with an axial slot in which there respectively engages one of the inclined arms of the eccentric V segment, while on the same side as the slot of one of the bristle-carrying bases, the other bristle-carrying base comprises a through hole for the transmission spindle of a size that will prevent interference between the corresponding bristle-carrying base and the arm of the V segment engaged in the slot of the other bristle-carrying base.

The amplitude of the oscillation of the reciprocating rotary motion of the two coaxial brushes making up the brushing head may be varied and made different for each brush by varying the inclination to the longitudinal axis of the drive shaft of the two inclined arms of the V-spindle.

The arms of the V segment of the transmission spindle may lie in the same plane parallel to the axis of rotation of the drive shaft. In this case the movements of the two brushes are in perfect phase opposition. The relationship between the phases of the oscillatory motions of the two brushes can be varied by giving one of the arms of the V segment of the transmission spindle a further inclination transversely to the plane containing the other arm.

The transmission for driving the two brushes of the brushing head in a reciprocating manner and in phase opposition is extremely simple and is easy to manufacture, and the work required is not of high precision. It ensures the least possible disturbance to operation in the event of wear and means that the construction of the brush involves a very few inexpensive parts that can be assembled easily and quickly.

By means of obvious and appropriate modifications, the transmission according to the invention can also be used to oscillate a brushing head having just one brush, by limiting the construction of the transmission spindle to a single inclined arm.

Similarly, if the brushing head is composed of more than two contrarotating parts, it is possible, by means of obvious modifications, to use the transmission spindle to drive all said parts, by giving it additional inclined segments, each being engaged in a slot in the corresponding part.

The invention also relates to other characteristics which further improve the toothbrush described above and these are covered by the dependent claims.

BRIEF DESCRIPTION OF THE DRAWINGS

The particular characteristics of the invention and the advantages procured thereby are dealt with in greater detail in the description of a preferred embodiment illustrated by way of non-restrictive example in the accompanying drawings, in which:

FIG. 1 is a perspective view of part of a toothbrush according to the invention.

FIG. 2 is an enlarged plan view of the brushing head of the toothbrush shown in FIG. 1.

FIG. 3 is an enlarged axial section of the end portion of the toothbrush handle and of the brushing head at its end.

FIG. 4 is an enlarged axial section of the brushing head alone, viewed in the direction of the axis of rotation of the drive shaft from the opposite side of the brushing head to said shaft.

FIG. 5 is an exploded perspective view of the brushing head shown in the previous Figures.

DESCRIPTION OF THE PREFERRED EMBODIMENT OF THE INVENTION

Figure 6:
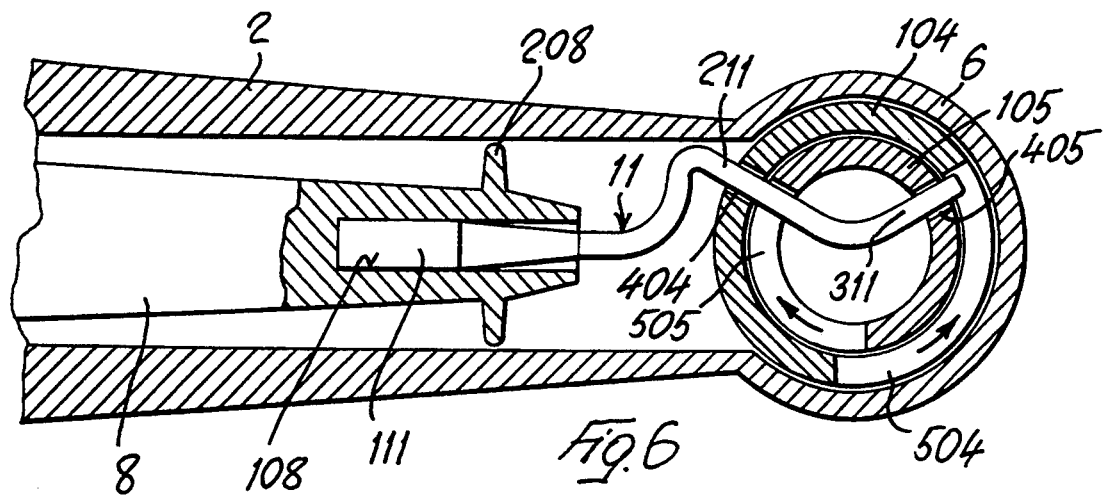
FIGS. 6 to 8 are sections through the brushing head and accompanying end portion of the shank taken through a plane perpendicular to the axis of rotation of said head, each showing the drive shaft and transmission spindle at a different angular position in the execution of a half-revolution.

The figures show an anti-plaque toothbrush comprising a handle part 1 to which there is axially and removably fitted a shank 2, ,whose free end carries a brushing head 3. The brushing head 3 is composed of a tubular outer brush 4 of cylindrical form and a circular inner brush 5. The two brushes 4 and 5 are supported coaxially in a cylindrical shell 6 integral with the shank 2 and are able to rotate relative to each other and with respect to the shell 6. The brushing head 3 is oriented so that its axis of rotation and bristles 7 are approximately perpendicular to the axis of the shank 2. The tubular brush 4 consists of a cylindrical bristle-carrying cup 104 which is housed freely rotatably in a complementary cavity 106 in the shell 6. The frontmost face of the cup 104 is formed by a radial widening or step 204 provided with axial holes 304 holding groups of bristles 7 and this widening or step rests on an internal annular shoulder 206 in the wall of accommodating cavity 106. Housed in the cylindrical bristle-carrying cup 104 is a hollow cylinder 105 which is the bristle-carrying element of the inner brush 5 and holds the bristle-carrying cup 104 in the cavity 106. The frontmost face of the bristle-carrying cylinder 105 is provided with axial holes 205 for holding groups of bristles 7.

The bristle-carrying cup 104 and cylinder 105 are held in the shell 6 by an element 13 which axially retains them. In the example illustrated, the retaining element comprises surfaces 413 which are held against the outermost face of the shell 6 and at least two or more axial retaining tongues 113, for example a ring of retaining tongues 113. The retaining tongues 113 possess hooked teeth 213 similar to saw teeth, and these point radially outwards and possess inclined surfaces 313 to facilitate their insertion. On the face of the head away from the bristles 7, the shell 6, the bristle-carrying cup 104 and the bristle-carrying cylinder 105 have central coinciding holes 306, 604, 605 in which the axial retaining tongues 113 are engaged. The diameter of the central hole 604 in the bristle-carrying cup 104 is less than the external diameter of the bristle-carrying cylinder 105 and therefore forms an annular terminal flange against which the outer peripheral edge of said bristle-carrying cylinder 105 is held. Internally, the bristle-carrying cylinder 105 has an annular groove 705 into which the teeth 213 of the retaining element 13 snap when mounted. Thus the bristle-carrying cylinder 105 and hence the bristle-carrying cup 104 are secured axially but freely rotatably about their axis to the shell 6.

On diametrically opposite sides, the cup 104 and cylinder 105 have an axial slot 404, 405, respectively, while on the same side, coinciding with the axial slot 404, 405 of the bristle-carrying cup 104 and bristle-carrying cylinder 105, the other part 105, 104 has a generally circular hole 505, 504.

The shank 2 is tubular and houses rotatably within itself a coaxial drive shaft 8 which, at the end that fits into the handle 1, is provided with means 9 allowing it to be removably rotationally connected to a shaft 10 of a driving motor, preferably an electric motor, not shown, which is housed in the handle 1. The drive shaft 8 is conical and at the end nearest the brushing head 3 has a discoidal guiding flange 208 that interacts with the cylindrical internal wall of the shank 2 as a rolling bearing. The opposite end of the drive shaft 8 also has a discoidal flange 308 acting as a rolling bearing that interacts with the internal wall of the shank 2 and as a thrust bearing, said discoidal flange 308 being interposed between a radial widening or step 102 in the connection mouth of the shank 2 and the endmost rim of the corresponding male part 101 on the handle 1.

On the end nearest the brushing head 3, the drive shaft 8 is integrally connected in rotation to a transmission spindle 11. The connection may be achieved by means of, for example, a non-round axial connection seat 108 in the end of the drive shaft 8, into which a corresponding non-round connection end 111 of the transmission spindle 11 is introduced. The transmission spindle 11 has a V segment oriented perpendicularly to the axis of rotation of the drive shaft 8 and eccentrically with respect to said axis of rotation. The first inclined arm 211 of the V segment of the transmission spindle 11 engages in the axial slot 404 of the bristle-carrying cup 104 of the tubular outer brush 4, linking up through the hole 505 of the bristle-carrying cylinder 105 of the inner brush 5, more or less in the latter's axis of rotation, with the next arm 311 of the V segment, which inclines in the opposite direction and engages in the slot 405 of said bristle-carrying cylinder diametrically opposite the axial slot 404 of the bristle-carrying cup 104. The holes 504 and 505 of the bristle-carrying cup 104 and cylinder 105 are preferably circular and coaxial with the drive shaft 8 and their radius is such that the coinciding portions of the arms 211 and 311 of the V segment of the transmission spindle 11 which pass through them cannot interfere with the peripheral edges thereof during rotation.

Figure 7:
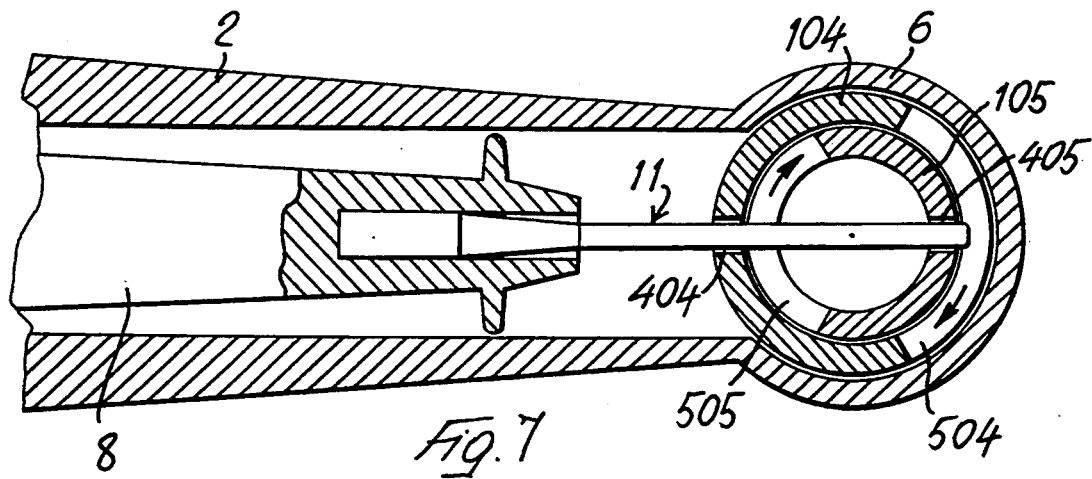
Figure 8:
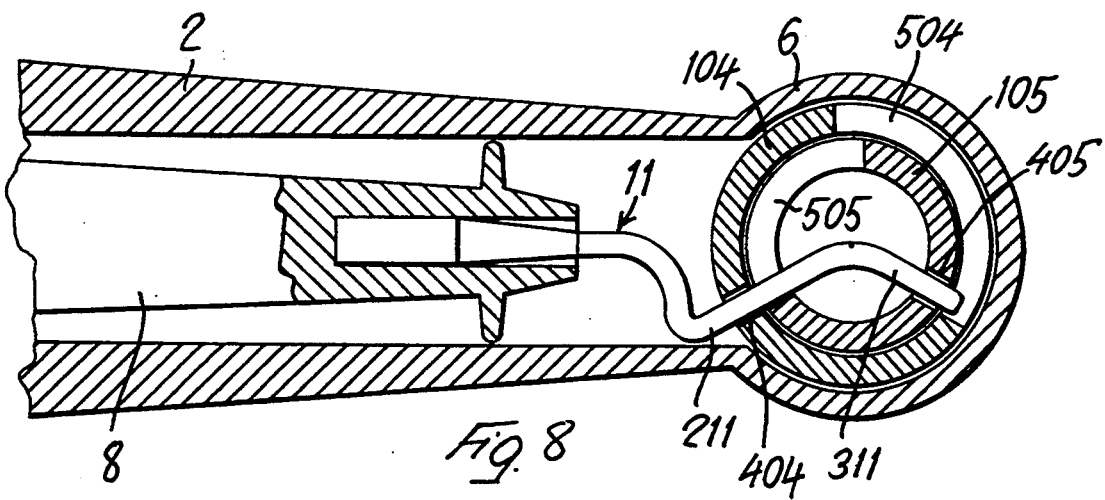

As is clear from FIGS. 6 to 8, in which three stages in a half revolution of the drive shaft 8 are illustrated, the arms 211, 311 engaged in the slots 404, 405 of the bristle-carrying cup and cylinder 104, 105 are free to execute a relative movement axially with respect to these, while they are engaged with the cup and cylinder 104, 105 peripherally, in consequence of which they cause them to rotate about their axis in opposite directions to each other. In the first half revolution of the drive shaft 8, the bristle-carrying cup 104 rotates anticlockwise, while the bristle-carrying cylinder 105 rotates clockwise. In the second half revolution, the directions of rotation of the bristle-carrying cup and cylinder 104, 105 are reversed. In this way a continuous rotation of the drive shaft 8 in one direction is converted by the transmission spindle 11 into a reciprocating rotation of the brushes 4, 5 in phase opposition.

As is easy to verify, if the two arms 211 and 311 of the transverse V segment of the transmission spindle 11 are inclined by equal but opposite angles to the axis of rotation of the drive shaft, the angular amplitude of the oscillatory stroke of the brushes 4 and 5 is essentially identical. The angular amplitudes can be varied by varying the absolute value of the angles of inclination of the arms 211 and 311. It is moreover possible to have the two brushes 4 and 5 execute oscillations in phase opposition with unequal angular amplitudes by giving the arms 211 and 311 of the transmission spindle 11 different absolute angles of inclination. Moreover, by additionally inclining one of the arms 211 or 311 of the transmission spindle 11 out of the common plane passing through these arms, the phase relationship between the oscillatory motions of the two brushes 4 and 5 is altered.

The particular construction of the toothbrush according to the invention means that the number of component parts can be limited to a maximum of 6, namely a supporting structure comprising in a single piece the tubular shank 2 and shell 6 for the brushing head 3, the two coaxial brushes 4 and 5, the retaining element 13, the drive shaft 8 and the transmission spindle. By designing the brushes 4 and 5 so that they hold axially to each other and to the shell 6, for example by means of complementary interconnecting annular shoulders and annular grooves, and by making the transmission spindle 11 integral with the drive shaft 8, the number of component parts is reduced to just four. Their construction is extremely simple, allowing simple manufacturing processes to be employed since no great dimensional accuracy is required of said parts.

Clearly the invention is not limited to the embodiments described above and illustrated but may be considerably varied and modified, especially in terms of construction. For example, the brushing head can be replaced by a different tool, such as a burnishing, polishing, massaging or other head. Moreover the particular construction of the transmission may also be employed in other similar types of devices requiring a continuous rotary motion to be converted into two reciprocating motions in phase opposition. Furthermore, by simply omitting the terminal inclined arm 311 of the transmission spindle 11, the transmission according to the invention can be adapted to convert the continuous one-way rotary motion into a reciprocating rotary motion of a one-piece tool head, such as a single-brush brushing head. All such changes may be made without abandoning the underlying principle described above and claimed below.

We claim:

1. A motorized anti-plaque toothbrush comprising:
   a tubular shaft;
   a handle removably connected to one end of said tubular shaft;
   an outer shell mounted on the other end of said tubular shaft;
   a brushing head mounted on the other end of said tubular shaft and rotatable about an axis approximately perpendicular to a longitudinal axis of the tubular shaft, said brushing head comprising at least two separate cleaning/massaging tool parts coaxially supported inside the outer shell and rotatable relative to each other;
   a drive shaft housed inside the tubular shaft;
   a motor housed inside the handle and dynamically connectable to the drive shaft for providing a continuous rotary motion to the drive shaft about a longitudinal axis perpendicular to the axis of rotation of the brushing head; and
   transmission means comprising a spindle rotatably coupled to the drive shaft and dynamically engaged with the brushing head for transmitting rotary motion from the drive shaft to the brushing head and converting the continuous rotary motion of the drive shaft into a reciprocating rotation of the tool parts in phase opposition to one another.

2. The toothbrush according to claim 1, wherein the transmission spindle comprises a shaft with bends.

3. The toothbrush according to claim 1, wherein said cleaning/massaging tool parts comprise a tubular outer brush and a central inner brush, said central inner brush being positioned coaxially inside said tubular outer brush, both of said brushes being positioned concentrically inside said outer shell, bristles of both the central inner brush and the tubular outer brush lying substantially parallel to the axis of rotation of the brushing head.

4. The toothbrush according to claim 3 wherein free ends of the bristles of the tubular outer brush and central inner brush terminate on a same surface.

5. The toothbrush according to claim 3 wherein the bristles of said tubular outer brush have a different length than the bristles of said central inner brush.

6. The toothbrush according to claim 3 wherein the transmission spindle comprises an eccentric V-shaped segment oriented transversely to the axis of rotation of the drive shaft and having its vertex in the axis of rotation of the tool parts, each of the tubular outer brush and central inner brush having a cylindrical bristle-carrying base rotatable about their common axis, each of said bristle-carrying bases having an axial slot and a through hole on a side opposite the axial slot, said central inner brush being positioned inside said tubular outer brush such that the axial slot of said central inner brush engages one of the inclined arms of said eccentric V-shaped segment and the axial slot of said tubular outer brush engages the other of the inclined arms of said eccentric V-shaped segment, each of said through holes having a sufficient size for preventing interference between its respective base and the axial slot of the other base.

7. The toothbrush according to claim 6, wherein angles formed by each of the two arms of the V-shaped segment of the transmission spindle with the axis of rotation of the drive shaft are equal for providing equal angular amplitudes of the oscillatory motions of the central inner brush and the tubular outer brush.

8. The toothbrush according to claim 6, wherein angles formed by each of the two arms of the V-shaped segment of the transmission spindle with the axis of rotation of the drive shaft are different for providing different angular amplitudes of the oscillatory motions of the central inner brush and the tubular outer brush.

9. The toothbrush according to claim 6, wherein the two arms of the V-shaped segment of the transmission spindle lie in a plane parallel to the axis of rotation of the drive shaft.

10. The toothbrush according to claim 9 wherein a portion of one of the two arms is inclined away from the plane.

11. The toothbrush according to claim 6, wherein the bristle-carrying base of the tubular outer brush comprises a cylindrical cup and the bristle-carrying base of the inner brush comprises a hollow cylinder, the cylindrical cup being housed rotatably in a complementary cylindrical seat inside the outer shell and the hollow cylinder being housed rotatably in a complementary cylindrical space inside the cylindrical cup, said toothbrush further comprising retaining means extending through coinciding holes in the base portion of said hollow cylinder, said cylindrical cup and said outer shell for locking said hollow cylinder axially and rotatably to the cylindrical seat and locking the cylindrical cup axially and rotatably between said cylindrical seat and said hollow cylinder.

12. The toothbrush according to claim 11, wherein the retaining means includes a first end having a surface for engaging the outer shell and a second end comprising at least two elastic axial retaining tongues having axially securing teeth at their ends for engaging an internal annular groove in said hollow cylinder by means of the axially securing teeth.

13. The toothbrush according to claim 12, wherein the coinciding holes in the cylindrical cup and hollow cylinder are coaxial and circular, the diameter of the hole in the cylindrical cup being less than the external diameter of the hollow cylinder.

14. The toothbrush according to claim 1, wherein the drive shaft includes an integral, radial extension at each end thereof which act as at least one of a roller bearing and a thrust bearing.

15. The toothbrush according to claim 14, wherein said drive shaft has a conical shape and tapers toward the brushing head, and wherein said radial extension at the end nearest the brushing head interacts with an internal wall of the tubular shaft and the radial extension at the opposite end comprises a thrust bearing positioned between a radial widening of an internal diameter of the tubular shaft and an end of the handle connected to the tubular shaft.

* * * * *